US00PP25822P3

(12) United States Plant Patent
Schoone

(10) Patent No.: US PP25,822 P3
(45) Date of Patent: Aug. 18, 2015

(54) ***PHALAENOPSIS* ORCHID PLANT NAMED 'MOONDANCE'**

(50) Latin Name: *Phalaenopsis hybrida*
Varietal Denomination: Moondance

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 123 days.

(21) Appl. No.: 13/986,291

(22) Filed: Apr. 19, 2013

(65) Prior Publication Data

US 2013/0291248 P1 Oct. 31, 2013

Related U.S. Application Data

(60) Provisional application No. 61/638,448, filed on Apr. 25, 2012.

(30) Foreign Application Priority Data

Apr. 26, 2012 (NL) ..... PBR OPS894

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
CPC ..... A01H 5/02; A01H 5/00
See application file for complete search history.

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'Moondance' particularly characterized by flowers which are white with large purple marks; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Moondance'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Moondance'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Moondance' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Moondance' originated from a cross made by the inventor in 1999 in Strengweg, Heemskerk, The Netherlands. The female or seed parent is the *Phalaenopsis* cultivar designated 'Tzeng-Wen Sentra', unpatented. The male or pollen parent is the *Phalaenopsis* cultivar designated 'Cygnus', unpatented. The new *Phalaenopsis* 'Moondance' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture (mericloning) was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Moondance', which in combination distinguish this *Phalaenopsis* as a new and distinct cultivar:

1. flowers which are white with large purple marks;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Moondance', the female parent 'Tzeng-Wen Sentra' has red/purple flowers and the male parent 'Cygnus' has white colored flowers, whereas the flowers of 'Moondance' are white with large purple marks Presently, the commercial cultivars to which 'Moondance' can be meaningfully compared are 'Everly Bear' (U.S. application Ser. No. 13/986,292) and 'Gold City' (U.S. application Ser. No. 13/986,295). The shape of the petals and sepals and the amount of purple marks of the three plants differ. The petals and sepals of 'Gold City' are more ovate/rounder than the petals and sepals of 'Everly Bear' and 'Moondance'. 'Gold City' has the least purple marks. Mainly around the center. 'Everly Bear' has beyond that also a striking large mark on its dorsal sepal. 'Moondance' has even more marks on the petals and sepals than 'Everly Bear'.

BRIEF DESCRIPTION OF THE PHOTOGRAPHS

The accompanying photographs illustrate the overall appearance of the new *Phalaenopsis* 'Moondance' showing the colors as true as is reasonably possible with colored reproductions of this type. Colors in the photographs may differ slightly from the color values cited in the detailed botanical description, which accurately describe the color of 'Moondance'.

DETAILED BOTANICAL DESCRIPTION

Figure 1:
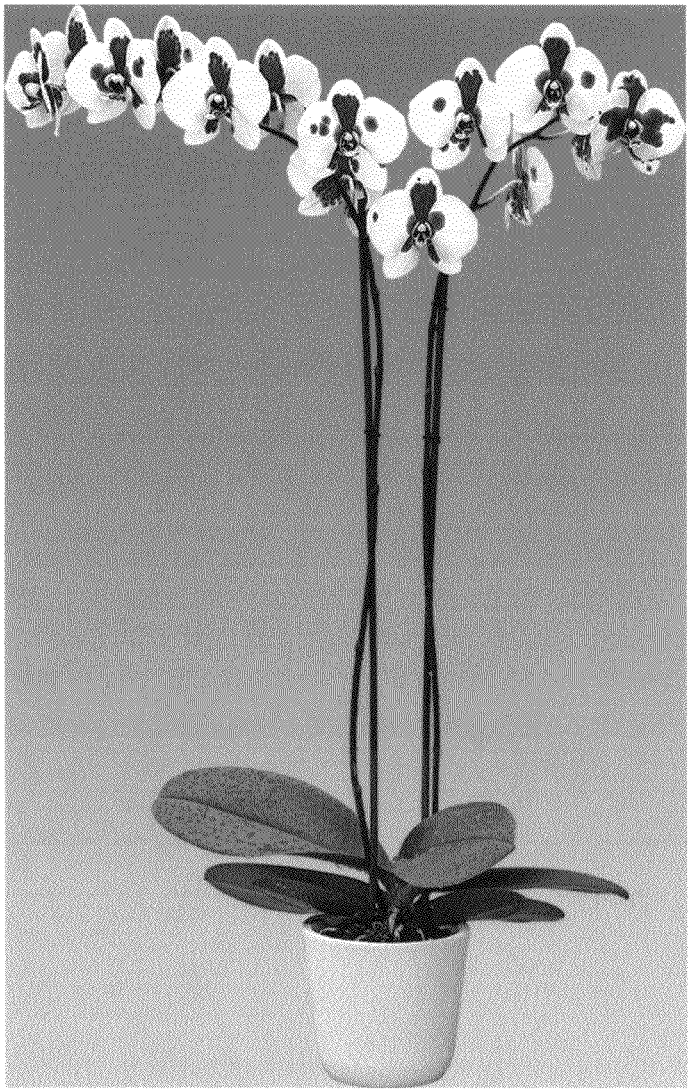
FIG. 1 shows a side view perspective of a typical flowering plant of 'Moondance' in a 12 cm pot, at 16 months of age.

The new *Phalaenopsis* cultivar 'Moondance' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Moondance' as grown in a greenhouse in Strengweg, Heemskerk, The Netherlands, under conditions which closely approximate those generally used in commercial practice. Initially, the ideal temperature to grow plants of 'Moondance' is 27° C. during the day and at night. Then, during the flowering phase of 'Moondance', the ideal growing temperature is 20-22° C. during the day and 18° C. at night. Light levels for growing 'Moondance' are a minimum of 5,000 lux and a maximum of 10,000 lux. A balanced fertilizer with level of 200 ppm N, 87 ppm P, 168 ppm K is applied. Duration of growth of 'Moondance' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Moondance' plants described is 12 months after potting.

Classification:

*Botanical.*—*Phalaenopsis hybrida.*

Parentage:

*Female or seed parent.*—*Phalaenopsis* cultivar designated 'Tzeng-Wen Sentra', unpatented.

*Male or pollen parent.*—*Phalaenopsis* cultivar designated 'Cygnus', unpatented.

Propagation:

*Type.*—Tissue culture.

*Rooting habit and description.*—Fleshy; approximately 4 mm-6 mm wide and green in color (RHS 163B); freely branching. It takes 12 weeks for plants growing in tissue culture to initiate roots.

Plant:

*Size at maturity.*—Height: about 65 cm. Spread: about 65 cm.

*Growth habit.*—Large; green leaves (RHS N137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:

*Quantity per plant.*—About 5 to 6 leaves are produced before flowering.

*Arrangement and attachment.*—Half up/horizontal and on two sides.

*Overall shape of leaf.*—Oval, the tip is blunt and asymmetric.

*Texture (upper & underside).*—Smooth and leathery.

*Pubescence.*—None.

*Mature leaf length.*—About 12 to 28 cm.

*Mature leaf width.*—About 6 to 10 mm.

*Mature leaf thickness.*—About 2 mm.

*Mature leaf color.*—Upper side: green (RHS N137A). Under side: green (RHS 137B).

*Leaf base.*—Acute.

*Margin.*—Entire.

*Venation.*—Pattern: parallel.

*Color of midvein.*—Upper side: green (RHS N137A). Under side: red/purple (RHS 137D).

Inflorescence description:

*Appearance.*—Upright to slightly pendant, racemose inflorescence with bilaterally symmetrical flowers that open in succession beginning with the lowermost flower.

*Buds.*—Height (from base to tip): about 31 mm. Diameter (at midpoint): about 25 mm. Shape: egg-shaped. Color: yellow/green (RHS 144B) with purple marks (RHS 79A).

*Raceme.*—Quantity per plant: about 1 to 2. Number of flowers per raceme: about 5 to 8. Length: about 60 to 80 cm.

*Peduncle.*—Diameter: about 3 to 6 mm. Strength: strong. Aspect: upright. Texture: glabrous and smooth. Color: green (RHS 137B).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with flower buds and flowers. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
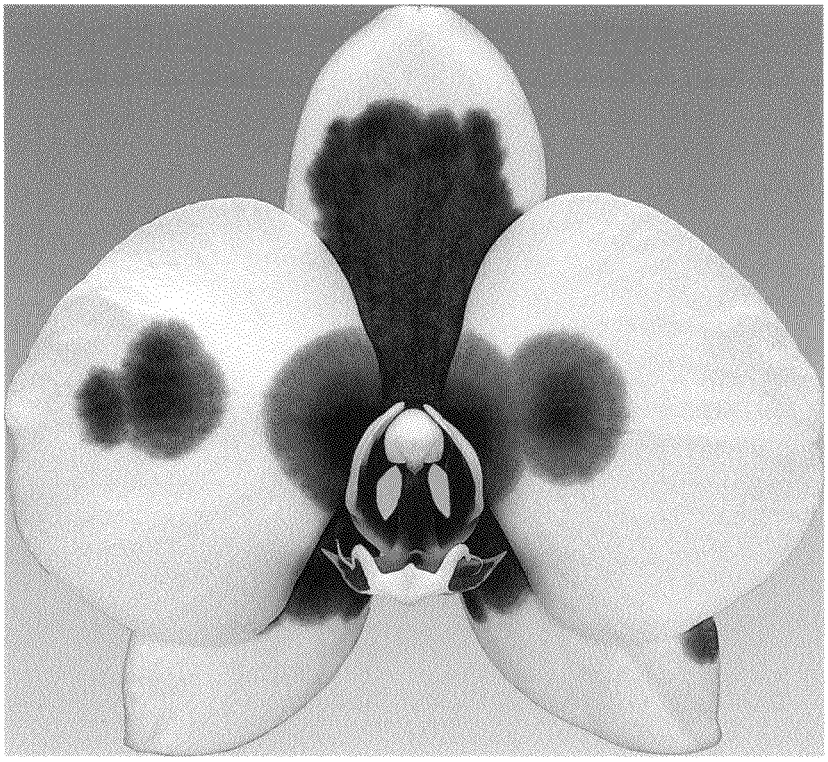
FIG. 2 shows a close-up view of a typical flower of 'Moondance'.
Figure 3:
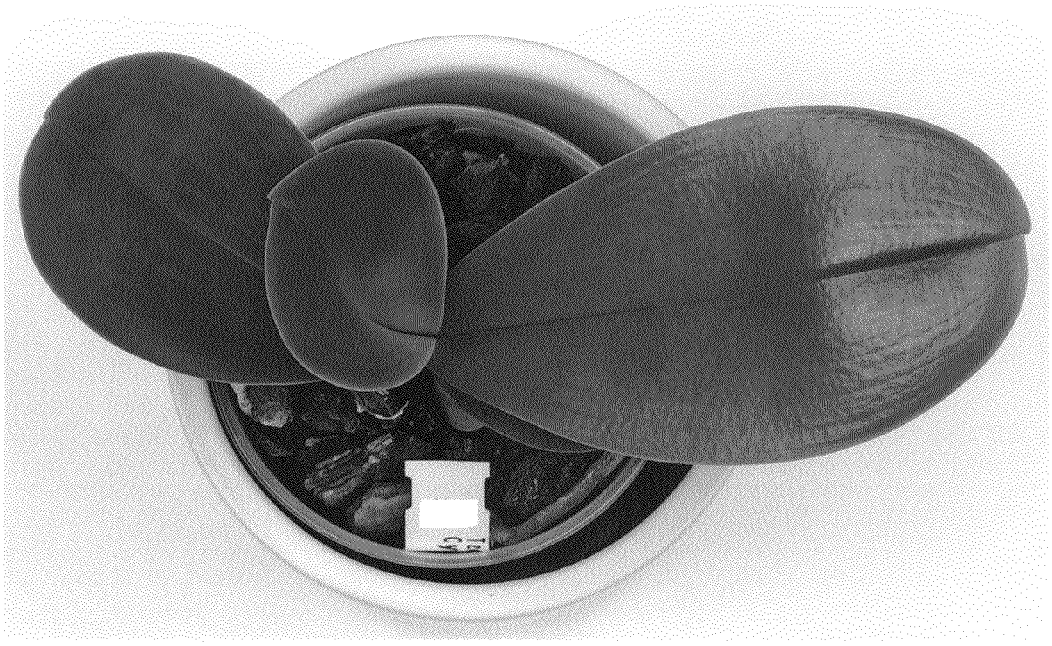
FIG. 3 shows a close-up view of the typical leaves of 'Moondance'.

*Flower.*—Rate of opening: Flowers fully opened about 2 to 3 days after petal and sepal separation. Orientation at opening: slanted upward and outward. Shape: typical shape of *Phalaenopsis* orchid; see FIG. 2. Size: Height: about 89 mm to 100 mm. Diameter: about 93 mm to 100 mm. Quantity and arrangement: three petals and three sepals that are trimerous, overlapping and arranged in 2 whorls. Petals are more pronounced than sepals.

*Petals.*—Arrangement: Inner whorl comprises 3 petals: 2 lateral petals and a labellum. 2 lateral petals: Overall shape: broadly ovate, bit triangular and weakly cupped. Apex: oval and weakly undulate. Margin: entire and weakly undulate. Base: broadly ovate. Length: about 55 mm. Width: about 45 mm. Texture: Upper surface: smooth and satiny. Under surface: smooth and satiny. Color (when fully opened): upper side: white/green (RHS 157B) with some white (155C). Some purple spots (RHS N79A) which are surrounded by lighter purple edges (RHS N78B). Under side: white/green (RHS 157A) with white (RHS 155C). Some purple spots (RHS N79A) which are surrounded by lighter purple edges (RHS N79D). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex: lateral lobes: oval. Midlobe: round corners. Length midlobe: about 21 mm. Width midlobe (not flattened): about 20 mm. Length lateral lobe: about 18 mm. Width lateral lobe (not flattened): about 12 mm. Depth of tube created from lateral lobes of labellum: about 12 mm. Texture: Upper and under surface: smooth and satiny. Color (when fully opened): Midlobe: upper surface: At the base yellow (RHS 6B), grey/purple (RHS 187B) on the sides and a line in the center. In between some red/purple (RHS 72B) and at the end some white (RHS NN155B). Under surface: At the base some yellow (RHS 6B) edges in the corners, than grey/purple (RHS 187B) which runs into red/purple (RHS 72B). In the center from base to cirrhi a white band (RHS NN155B). Lateral lobes: upper surface: At the base grey/purple (RHS 187A) which runs into red/purple (RHS 72B). At the top white (RHS NN155B) and lower edge is yellow (RHS 13A). Under surface: at the base some white (RHS N155A), which runs into grey/purple (RHS 187A). At the top a small edge of red/purple (RHS 72B). The upper half is white (RHS NN155B) and the lower half is yellow (RHS 13A). Cirrhi: long (about 15 mm) and wavy. Color: white (RHS NN155B) with yellow tips (RHS 13B). Pestle (Callosities): Length: about 4 mm. Width (not flattened): about 3 mm. Color: Top is grey/purple (RHS N187B), sides are grey/yellow (RHS 162A). On the front there is a grey/purple (RHS N187A) line down the middle.

*Sepals.*—Arrangement: Outer whorl comprises 3 sepals: one dorsal and two lateral sepals. Overall shape: elliptical and weakly cupped. Margin: entire and weakly undulate. Length: about 47 mm. Width: about 31 mm. Apex: dorsal: round/oval lateral: oval tapering to a point. Texture: Upper and under surface: smooth and satiny. Color (when fully opened): upper surface: main color dorsal sepal is white (RHS 155C) with green/white (RHS 157B) and lateral sepals is green/white (RHS 157A). Both have purple marks (RHA N79A) surrounded by a purple rim (RHS N78B). Under surface: main color lateral sepals is yellow/green (RHS 149D with RHS 149C) and dorsal sepal is white (RHS 155C and RHS 149B). They both have purple marks (RHS N79B with RHS N79C).

Pedicel.—Length: about 45 to 52 mm. Diameter: about 4 mm. Texture: glabrous and smooth. Color: from yellow/green (RHS 149D) into purple (RHS N77C) into grey/purple (RHS N186A).

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—Length: about 9 mm. Diameter: about 6 mm. Color: white (RHS NN155B) with at the base little red/purple (RHS N74A) which runs into RHS N74D.

*Pollinia.*—Quantity: two. Diameter: about 1 mm. Color: orange (RHS 24B).

*Ovary.*—Length: about 3 mm. Diameter: about 1.5 mm. Color: white (RHS NN155B).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Moondance', as illustrated and described herein.

* * * * *